United States Patent
Yan et al.

(10) Patent No.: US 11,542,474 B2
(45) Date of Patent: Jan. 3, 2023

(54) RECOMBINANT ADIPOSE-DERIVED STEM CELL AND RECOMBINANT METHOD THEREOF

(71) Applicant: North China University of Science and Technology, Hebei (CN)

(72) Inventors: Zhenyu Yan, Hebei (CN); Linhong Wang, Hebei (CN); Yanyan Xie, Hebei (CN); Xin Wang, Hebei (CN)

(73) Assignee: North China University of Science and Technology, Tangshan (CN)

( * ) Notice: Subject to any disclaimer, the term of this patent is extended or adjusted under 35 U.S.C. 154(b) by 571 days.

(21) Appl. No.: 16/668,065

(22) Filed: Oct. 30, 2019

(65) Prior Publication Data

US 2020/0362311 A1    Nov. 19, 2020

(30) Foreign Application Priority Data

May 15, 2019  (CN) .......................... 201910405750.X

(51) Int. Cl.
| | | |
|---|---|---|
| *C12N 5/0775* | (2010.01) | |
| *C12N 15/86* | (2006.01) | |
| *C12N 15/87* | (2006.01) | |

(52) U.S. Cl.
CPC ........... *C12N 5/0667* (2013.01); *C12N 15/86* (2013.01); *C12N 15/87* (2013.01)

(58) Field of Classification Search
None
See application file for complete search history.

(56) References Cited

U.S. PATENT DOCUMENTS

2011/0225661 A1* 9/2011 Deng ................. A61K 48/0008
800/9

OTHER PUBLICATIONS

Watanabe, et al. (2013) "Genetically Modified Adipose Tissue-Derived Stem/Stromal Cells, Using Simian Immunodeficiency Virus-Based Lentiviral Vectors in the Treatment of Hemophilia B", Human Gene Therapy, 24: 283-94. (Year: 2013).*
Zhang, et al. (2018) "Netrin-1 improves adipose-derived stem cell proliferation, migration, and treatment effect in type 2 diabetic mice with sciatic denervation" Stem Cell Research & Therapy, 9: article 285, 13 pages long. (Year: 2018).*
Sharma, et al. (2016) "Adeno-Associated Virus 5 Transduces Adipose-Derived Stem Cells with Greater Efficacy Than Other Adeno-Associated Viral Serotypes", Human Gene Therapy Methods, V. 27, No. 6, pp. 219-227. (Year: 2016).*
Hartmann, et al. (2007) "Adenoviral infection induces a multi-faceted innated cellular immune response that is mediated by the toll-like receptor pathway for A549 cells" Virology, 358: 357-72. (Year: 2007).*
Yan, et al. (2020) "Adenovirus Mediates Expression of Human Coagulation Factor IX Gene in Adipose-Derived Mesenchymal Stem Cells" [Abstract], International Society on Thrombosis and Haemostasis, 4(Suppl 1), Abstract No. PB1093, 2 pages. (Year: 2020).*
Wang, et al. (2020) "Expression of Adenovirus-Mediated Factor IX Gene in Mouse Adipose-derived Stem Cells", Zhongguo Shi Yan Xue Ye Xue Za Zhi, 28(5): 1718-25, Abstract Only (1 page). (Year: 2020).*

* cited by examiner

*Primary Examiner* — Robert M Kelly
(74) *Attorney, Agent, or Firm* — Tutunjian & Bitetto, P.C.

(57) ABSTRACT

The present invention provides a recombinant adipose-derived stem cell and a recombinant method thereof, and belongs to the technical field of genetic engineering, where an adenovirus carrying an hFIX gene is transfected into an adipose-derived stem cell to obtain the recombinant adipose-derived stem cell. In the present invention, an adenovirus carrying an hFIX gene is transfected into an adipose-derived stem cell, and the recombinant adipose-derived stem cell obtained after the transfection can express an hFIX protein.

6 Claims, 10 Drawing Sheets

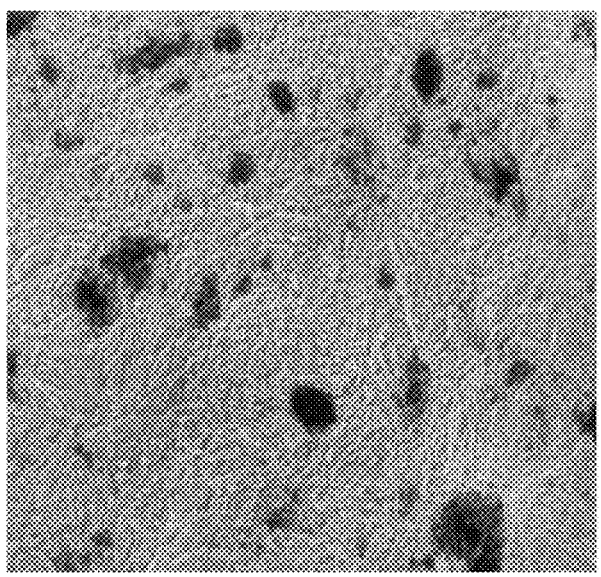 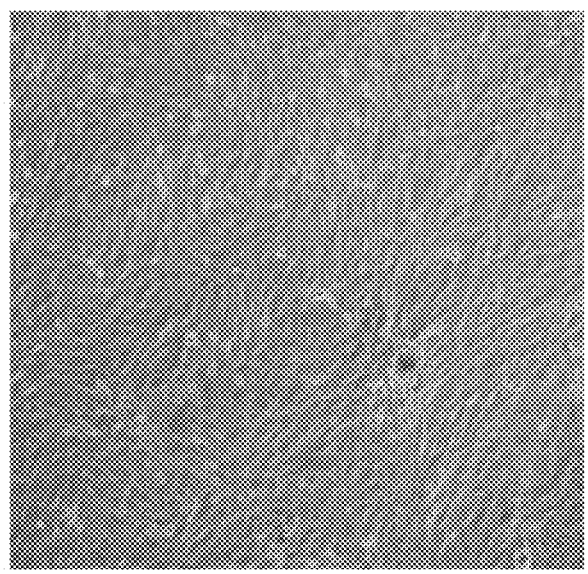
FIG. 1A                                    FIG. 1B

RECOMBINANT ADIPOSE-DERIVED STEM CELL AND RECOMBINANT METHOD THEREOF

This application claims priority to Chinese application number 201910405750.X, filed May 15, 2019, with a title of RECOMBINANT ADIPOSE-DERIVED STEM CELL AND RECOMBINANT METHOD THEREOF. The above-mentioned patent application is incorporated herein by reference in its entirety.

TECHNICAL FIELD

The present invention belongs to the technical field of genetic engineering, and in particular relates to a recombinant adipose-derived stem cell (ADSC) and a recombinant method thereof.

BACKGROUND

Hemophilia B is a hemorrhagic disease caused by a deficiency or malfunction of FIX, which is a X-linked recessive hereditary disease. The severity of the disease is related to the degree of FIX deficiency. According to the level of FIX activity in a patient with hemophilia B, the patient can be divided into three categories: being of a serious type when a coagulation factor IX Activity (FIX:C) <1%; being of an intermediate type when 1%≤FIX:C≤5%, and being of a mild type when 5%≤FIX:C≤40%. The incidence of this disease among male newborns is about 1/25,000. It is estimated that the total number of patients with hemophilia B in China is about 20,000, accounting for 15%-20% of the total number of hemophilia patients. At present, hemophilia B is mainly clinically treated with an alternative therapy, that is, achieving a therapeutic effect by restoring the level of coagulation factors in a patient's plasma through infusion of a recombinant blood-derived FIX (Factor IX, coagulation factor IX). The alternative therapy can effectively treat and prevent acute bleeding, but cannot prevent occurrence of joint injury, unless a prophylactic treatment begins in childhood. In developed countries it is generally recommend that a patient with serious hemophilia B is injected with FIX for 2-3 times a week. Due to the high cost of treatment, the majority of patients with hemophilia B in China are unable to receive normative treatment due to economic pressure.

There is no method of cure for hemophilia B, but the physiological characteristic of single gene inheritance makes it an ideal choice for gene therapy research. Numerous experimental studies at home and abroad have shown that a gene therapy for hemophilia B can increase the level of the coagulation factor IX, which makes it possible to cure hemophilia B.

The gene therapy pathway of hemophilia B can be divided into an in vivo pathway and an ex vivo pathway. The in vivo pathway refers to directly injecting a vector carrying a gene of interest into a patient. The method has the advantages of convenient operation, low cost, short treatment period, easy promotion, and represents the development direction of gene therapy. However, a strong immune response is easily caused in the patient after introduction of the carrier and the gene, and thus the method has a high safety risk, and some viral carriers cannot achieve the desired therapeutic effect as they are easily inactivated by serum complements in the patient. The ex vivo pathway refers to taking a somatic cell of the patient, and introducing the gene of interest into the somatic cell during in vitro culture, and then transfusing the genetically modified cell back to the patient. The method is relatively classic, safe and easy to control, basically does not cause immunological rejection of the patient and there is no problem that the virus is inactivated in the body. However, each time of gene therapy requires gene transferring, clone screening, and safety detecting, and thus the operation is cumbersome, the treatment cycle is long, the technology is complicated, and the cost is high.

The previous experiments of transduction of the FIX gene into different somatic cells in vitro successfully verify the in vitro expression of the FIX factor. However, the experimental results of transgenic treatment of hemophilia animals show that, the FIX factor expressed in vivo at a high level will have an expression quantity that decreases over time, which is mainly caused by the low efficiency of the gene delivery system itself and the immunogenic-response-mediated reduction in the expression quantity after the gene-modified cell expresses a transgene product.

SUMMARY

In view of the above, embodiments of the present invention provide a recombinant adipose-derived stem cell and a recombinant method thereof. In the present embodiments, an adenovirus carrying a human factor IX (hFIX) gene is transfected into an adipose-derived stem cell, and the recombinant adipose-derived stem cell obtained after the transfection can express an hFIX protein.

In order to achieve the foregoing invention results, the embodiments of the present invention provide the following technical solutions:

The embodiments of the present invention provide a recombinant adipose-derived stem cell, which is obtained by transfecting an adenovirus carrying an hFIX gene into an adipose-derived stem cell.

The embodiments of the present invention also provide a recombinant method of the recombinant adipose-derived stem cell described in the aforementioned technical solution, including:

when reaching 80% confluency of adipose-derived stem cells, mixing an adenovirus carrying an hFIX gene with an adipose-derived stem cell, and then conducting transfection to obtain a recombinant adipose-derived stem cell.

When a primary adipose-derived stem cell is passed to the 3rd generation, the cells of the 3rd generation can be transfected with an adenovirus carrying the hFIX gene.

The conditions of transfection can include:

the transfection temperature being 35-40° C., and the transfection time being 24-72 hours (h);

the transfection can be conducted under 5% $CO_2$;

the titer of the adenovirus carrying the hFIX gene can be $1.26 \times 10^{10}$ plaque forming units per milliliter (pfu/mL); and the adipose-derived stem cell expresses CD29 and CD90, and does not express CD45.

The present embodiments provide a recombinant adipose-derived stem cell and a recombinant method and application thereof. The present embodiments transfect the adenovirus carrying the hFIX gene into the adipose-derived stem cell to obtain the recombinant adipose-derived stem cell. In the present embodiments, an adenovirus carrying an hFIX gene is transfected into an adipose-derived stem cell, and the recombinant adipose-derived stem cell obtained after the transfection can express an hFIX protein.

BRIEF DESCRIPTION OF THE DRAWINGS

FIG. 1A shows the morphology of primary ADSCs observed under an inverted phase contrast microscope (×40);

FIG. 1B shows the morphology of the second generation of ADSCs observed under an inverted phase contrast microscope (×40);

DETAILED DESCRIPTION

Figure 2:
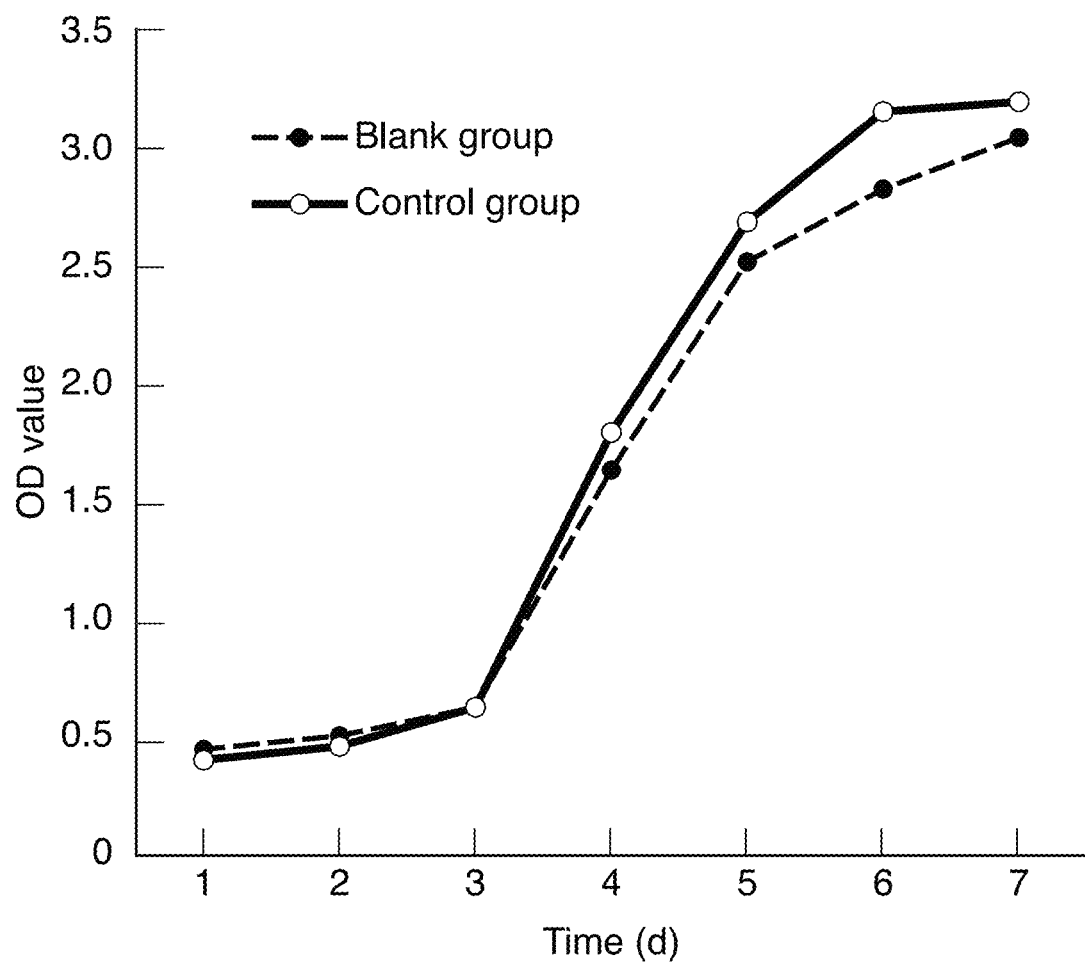
FIG. 2 is a growth curve of ADSC.

The present invention relates generally to a recombinant adipose-derived stem cell, which transfects an adenovirus carrying an hFIX gene into an adipose-derived stem cell to obtain the recombinant adipose-derived stem cell.

The embodiments of the present invention have no specific limitation on the preparation method of the adenovirus carrying the hFIX gene, and a conventional preparation method can be used. In the embodiments of the present invention, the adenovirus carrying the hFIX gene can be constructed by Hanbio Biotechnology Co., Ltd. In the embodiments of the present invention, the titer of the adenovirus carrying the hFIX gene can be about $1.26 \times 10^{10}$ pfu/mL.

The embodiments of the present invention have no specific limitation on the source of the adipose-derived stem cell, and the adipose-derived stem cell can be extracted and isolated from an adipose tissue, and the source of the adipose tissue may be a human adipose tissue or a murine adipose tissue. The embodiments of the present invention have no specific limitation on the method for acquiring the adipose-derived stem cell, and a conventional method can be employed.

In the embodiments of the present invention, when the primary adipose-derived stem cell is passed to the 3rd generation, the cells of the 3rd generation are transfected with an adenovirus carrying the hFIX gene. The embodiments of the present invention have no specific limitation on the method for passaging the primary adipose-derived stem cell, and a conventional method can be used.

In the embodiments of the present invention, the recombinant adipose-derived stem cell can be transferred into an animal without causing any immune response of the body, and is capable of continuously and efficiently expressing the hFIX protein. In embodiments of the present invention, the animal can be a mouse.

The embodiments of the present invention also provide a recombinant method of the recombinant adipose-derived stem cell described in the aforementioned technical solution, including: when reaching 80% confluency of adipose-derived stem cells, mixing an adenovirus carrying an hFIX gene with an adipose-derived stem cell, and then conducting transfection to obtain a recombinant adipose-derived stem cell.

In embodiments of the present invention, the transfection conditions can include that: the transfection temperature is 35-40° C., or 37° C.; and the transfection time can be 24-72 h. In embodiments of the present invention, the transfection can be carried out under 5% carbon dioxide ($CO_2$).

The embodiments of the present invention can use a cell culture flask and a complete medium to culture the adipose-derived stem cells of the 3rd generation. The embodiments of the present invention have no specific limitation on the specification and the source of the cell culture flask, and a conventional cell culture flask can be employed. In embodiments of the present invention, the complete medium can be a DMEM medium containing 10% FBS and 1% of a bispecific antibody. The embodiments of the present invention have no particular limitation on the source of the DMEM medium, and a commercially-available product conventional in the art may be used.

In embodiments of the present invention, the adipose-derived stem cell of the 3rd generation can express CD29 and CD90, but may not express CD45.

In embodiments of the present invention, whether a recombinant adipose-derived stem cell is obtained is proven by detecting the fluorescent expression condition of the transfected adipose-derived stem cell. If green fluorescence is detected, it indicates that the adenovirus carrying the hFIX gene is successfully transfected into the adipose-derived stem cell, and the recombinant adipose-derived stem cell is obtained.

The technical solution provided by the present invention will be described in detail in connection with the following embodiments, but they should not be construed as limiting the claimed scope of the present invention.

Embodiment 1

1.4 C57 mice of 3-4 weeks old were taken (purchased from Beijing Huafukang Bioscience Co., Ltd.), sacrificed by cervical dislocation, and then soaked in 75% alcohol for 15 min. The adipose tissues of the mice at the inguinal region were bluntly dissected on a super clean bench (a clean bench, also called a laminar flow bench or laminar flow workstation, is a piece of equipment designed to create a micro-environment that meets industry standards for a particular control), rinsed in a phosphate-buffered saline (PBS) buffer for 3 times to remove blood vessels and hairs that were visible by naked eyes, and then the adipose tissues were cut into blocks of a size of about 4 $mm^2$, and placed into a 50 ml centrifuge tube. The adipose tissues were digested in a water bath kettle containing 3 volumes of 0.1% of collagenase I for about 1 h by shaking manually. The digestion condition of the adipose tissues was observed while shaking, and when no massive microstructure is visible by naked eyes, equivalent volumes of a DMEM-F12 medium (Dulbecco's Modified Eagle Medium/Nutrient Mixture F-12) containing 10% fetal bovine serum (FBS) and 1% of a Penicillin-Streptomycin bispecific antibody was added and mixed well to terminate the digestion. The digested emulsion was filtered through a 70 um (200 mesh) cell mesh filter, the filtered liquid was centrifuged at 800 rmp for 5 min, the upper layer of fat and supernatant were discarded, and the cell pellet was resuspended using 5 ml of a DMEM-F12 medium containing 10% FBS and 1% of the Penicillin-Streptomycin bispecific antibody, and inoculated in a 25 $cm^2$ culture flask and cultured in an incubator containing $CO_2$ at the volume fraction of 5% at 37° C. After 72 h, the medium was replaced for the first time, and thereafter the medium was replaced once every 2-3 days. The cells, when 90% confluency was reached, were digested with 500 ul of 0.25% trypsin for 1 min, added with 2 ml of the aforementioned complete medium to terminate the digestion, the liquid was pipetted and centrifuged at 800 rpm for 5 min, and the cells were resuspended in the complete medium and subcultured at 1:2.

2. The cell morphology was observed under the inverted phase contrast microscope. The primary cells adhered to the wall at about 8 h with the cells being round and having strong refractivity, and afterwards, the cells gradually changed into long-shuttle and dendritic shapes and were arranged in clusters with tiny tissue blocks as centers. (FIG. 1A-1B). The cells had increased volumes and increased antennas after passage, and the cells aged and disintegrated when passed to approximately the 10th generation.

3. The ADSCs of the 3rd generation were taken, digested with 0.25% trypsin and then counted, prepared into a single-cell suspension with the cell density being adjusted to $2\times10^3$/well and inoculated into a 96-well plate, where 6 replicate wells were set, and cells were inoculated in 7 plates in total. The cells were cultured in an incubator containing 5% $CO_2$ at 37° C. 1 plate was taken at a fixed time each day, the old medium was discarded, and each well was added with 10 microliters (ul) of a CCK-8 reagent+100 ul of the complete medium. The cells were incubated in the incubator for 1 h and then measured for the absorbance on a microplate reader for 7 days in total. A growth curve was drawn by using the time as the abscissa and using the OD value as the ordinate. The ADSC growth curve was inverted-S-shaped, which was consistent with the general cell growth principle (FIG. 2).

Figure 3A:
FIG. 3A shows formation of lipid droplet after adipogenic induction of ADSCs at (×40)
Figure 3B:
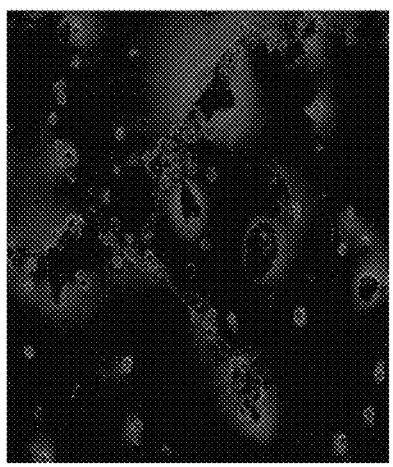
FIG. 3B shows formation of lipid droplet after adipogenic induction of ADSCs at (×100)
Figure 3C:
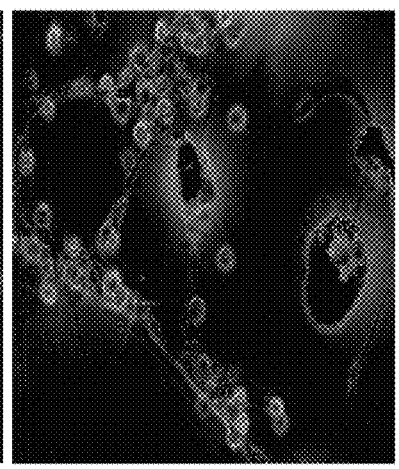
FIG. 3C shows formation of lipid droplet after adipogenic induction of ADSCs at (×200)

4. The ADSCs of the 3rd generation were taken and inoculated in 2 12.5 $mm^2$ culture flasks, and were respectively added with an adipogenic induction solution and an osteogenic induction solution when 50% confluency was reached. The induction solutions were replaced once each 2-3 days, and the cells were induced for 9 days in total. The induced cells were stained with oil red O and alizarin red staining kits respectively. Red lipid droplets and red osteogenic nodules were observed under the inverted phase contrast microscope, indicating that adipogenic induction of the ADSCs was successful and had a multipotential differentiation potential (FIG. 3A-3C, where 3A: ADSCs (×40), 3B: ADSCs (×100), 3C: ADSCs (×200)).

Figure 4A:
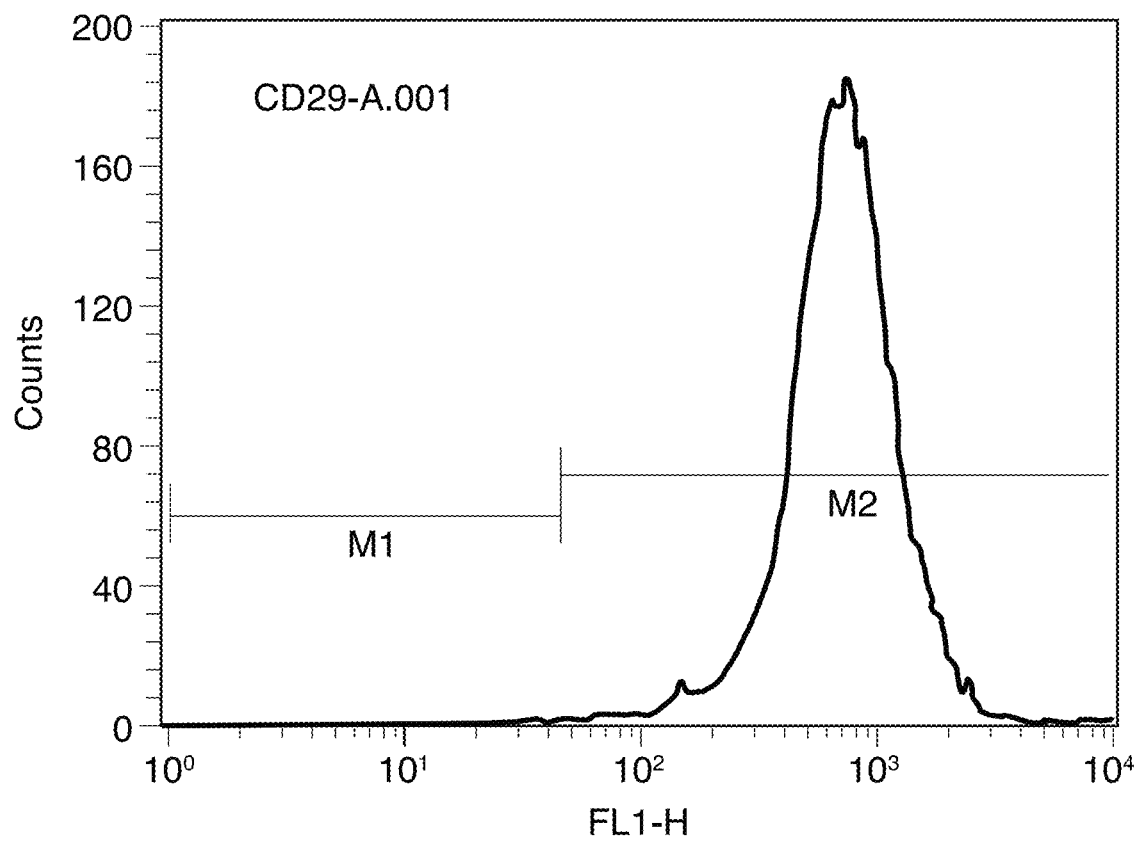
FIG. 4A shows the phenotypic results of ADSCs of CD29.
Figure 4B:
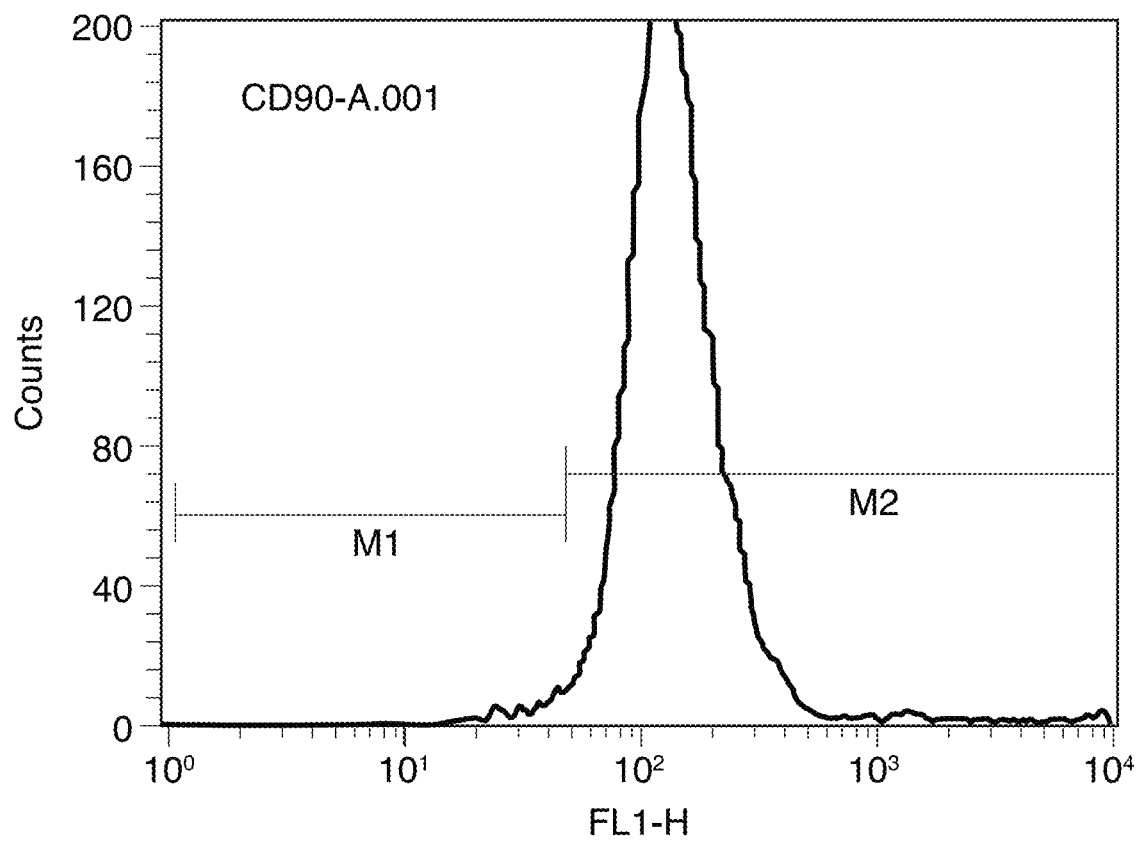
FIG. 4B shows the phenotypic results of ADSCs of CD90.
Figure 4C:
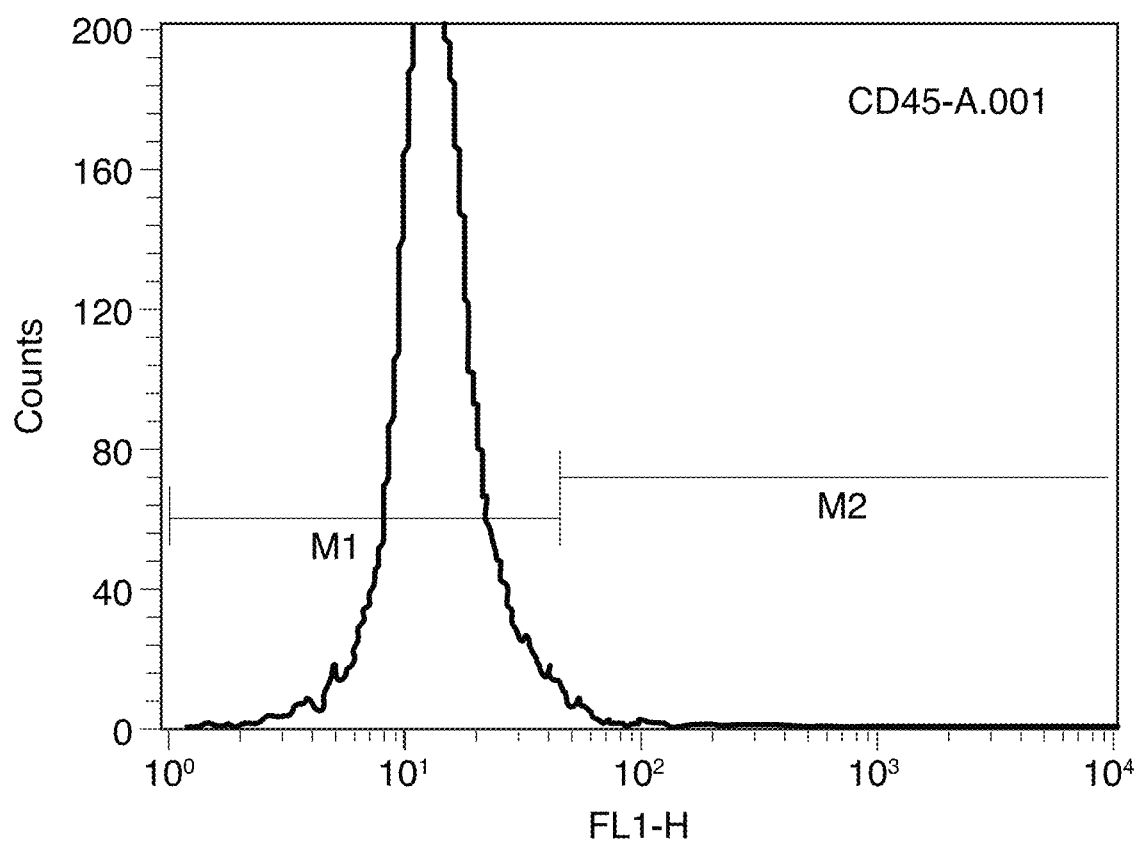
FIG. 4C shows the phenotypic results of ADSCs of CD45.

5. The ADSCs of the 3rd generation were taken, and prepared into a single-cell suspension by digesting in 0.25% trypsin through flow cytometry, centrifuged and then rinsed with PBS for 2 times, the cell concentration was adjusted to $1\times10^6$/tube, and the cells were added with 2 ul of CD-29FITC, CD-90FITC, CD-45FITC antibodies respectively, incubated at 4° C. with protection from light for 30 min, and detected through a flow cytometer. The results showed that, the cells highly expressed CD29 and CD90, and did not express CD45 (FIG. 4A-4C). The ADSCs highly expressed CD29 (99.91%) (FIG. 4A) and CD90 (99.02%) (FIG. 4B), and hardly expressed CD45 (0.94%) (FIG. 4C).

After the aforementioned morphology observation, cell growth curve determination, multipotential differentiation potential determination and flow-cytometry phenotype identification of the ADSCs, it could be proved that the primary ADSCs were successfully extracted and cultured, the ADSCs of the 3rd generation had stronger growth ability and differentiation potential, and high purity, so that the ADSCs of the 3rd generation were taken for transfection.

Embodiment 2

Figure 5A:
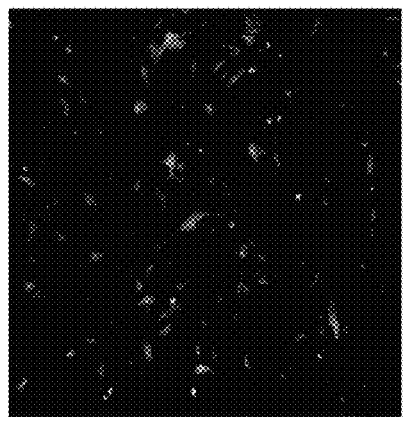
FIG. 5A shows ADSCs that express green fluorescence, i.e., ADSCs successfully transfected with the adenovirus, for transfection for 24 h.
Figure 5B:
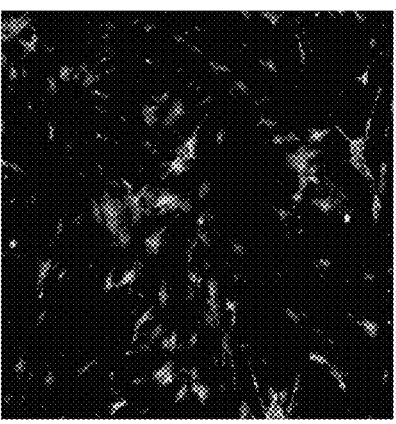
FIG. 5B shows ADSCs that express green fluorescence, i.e., ADSCs successfully transfected with the adenovirus, for transfection for 48 h.
Figure 5C:
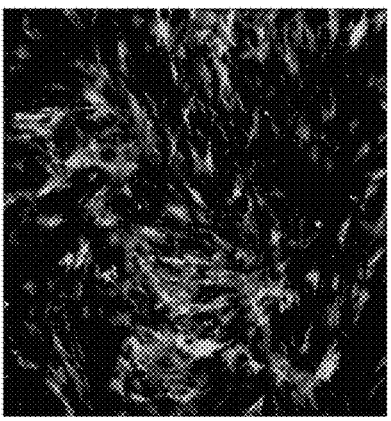
FIG. 5C shows ADSCs that express green fluorescence, i.e., ADSCs successfully transfected with the adenovirus, for transfection for 72 h.

When confluency of the ADSCs of the 3rd generation as prepared in Embodiment 1 was 80%, the old medium was discarded, and 4 ml of a fresh complete medium (the DMEM medium containing 10% FBS and 1% of the bispecific antibody) was added. To obtain MOI=300, about 24 ul of a stock of viruses carrying the hFIX gene at a titer of $1.26\times10^{10}$ pfu/mL (constructed by Hanbio Biotechnology Co., Ltd.) was pipetted and added into a cell culture flask, mixed well, and cultured in an incubator containing 5% $CO_2$ at 37° C. for 12 h, then the virus-containing medium was discarded, replaced with 5 ml of a refresh complete medium, and the cells were continually incubated in the incubator containing 5% $CO_2$ at 37° C. The expression conditions of green fluorescence were observed respectively at 24 h, 48 h and 72 h. It was observed that the expression of the green fluorescence was strong at 24 h, and the green fluorescence was stronger at 48 h and 72 h than that at 24 h, and had an increased expression rate up to more than 90%. The ADSCs capable of expressing the green fluorescence were the ADSCs successfully transfected with adenoviruses, such that the recombinant adipose-derived stem cells were obtained (FIG. 5A-5C, for transfection for 24 h, 48 h, and 72 h, respectively).

Embodiment 3

Figure 6:
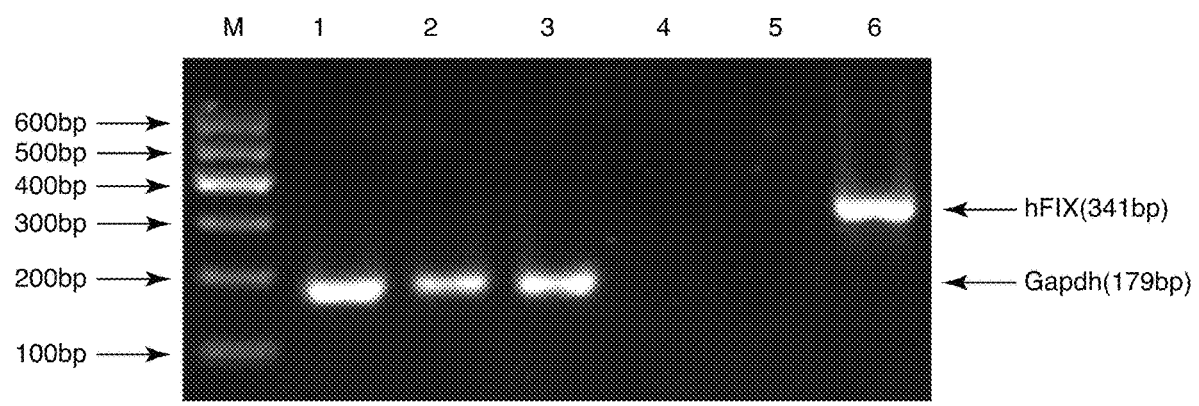
FIG. 6 shows the imaging results of RT-PCR agarose gel electrophoresis, where M is marker, 1 is a blank group, 2 is an empty-vector group, 3 is a recombinant adipose-derived stem cell group, 4 is a blank group, 5 is an empty-vector group, and 6 is a recombinant adipose-derived stem cell group.

Cell RNAs were respectively extracted from 3 groups, i.e., the ADSCs that had been transfected with viruses carrying the hFIX gene for 48 h, transfected with empty viruses for 48 h, and not transfected with viruses. By Reverse Transcription-Polymerase Chain Reaction (RT-PCR) agarose gel electrophoresis, the expression of the hFIX mRNA could be detected in the group transfected with viruses carrying the hFIX gene (the recombinant adipose-derived stem cells obtained in Embodiment 2), but not detected in the group transfected with empty viruses and the group that was not transfected with viruses (FIG. 6). It could be concluded from FIG. 6 that, the group of recombinant adipose-derived stem cells has expressed an hFIX-specific fragment of 341 bp in length, while no expression strap was seen in either the empty virus group or the blank group. The Gapdh reference gene fragment was amplified in cells of each of the three groups.

Figure 7:
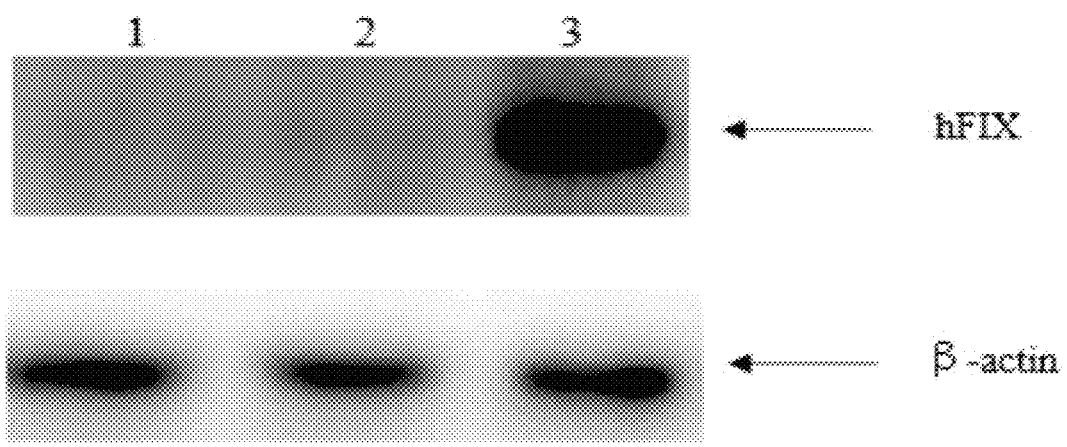
FIG. 7 shows the results of Western blot detection, where 1 is a blank group, 2 is an empty-vector group, and 3 is a recombinant adipose-derived stem cell group.

The proteins were respectively extracted from the aforementioned 3 groups of adipose-derived stem cells. By Western blot, the expression of the hFIX protein was detected in the group transfected with viruses carrying the hFIX gene (i.e., the recombinant adipose-derived stem cells), and no expression of the hFIX protein was detected in the other two groups (FIG. 7).

Figure 8:
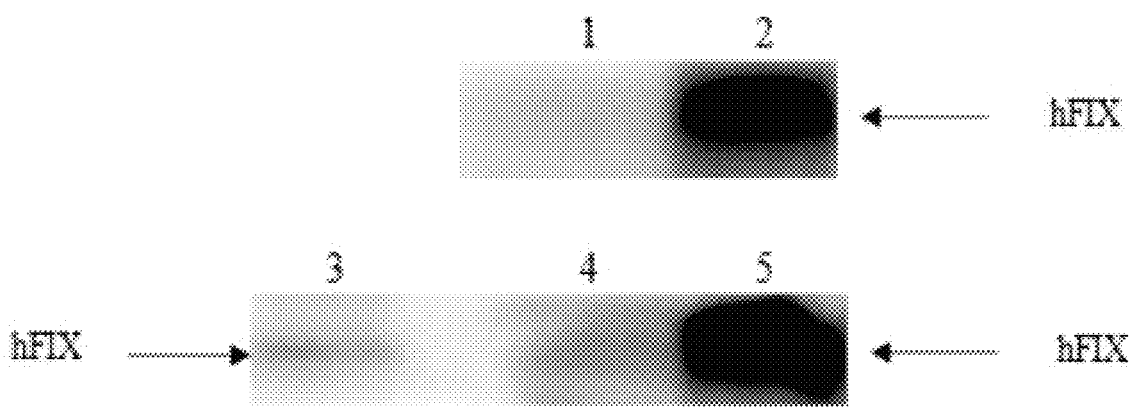
FIG. 8 shows the results of Western blot detection, where 1 is a supernatant of the blank group, 2 is a supernatant of the recombinant adipose-derived stem cell group, 3 is an internal protein of the recombinant adipose-derived stem cell, 4 is a supernatant of the blank group, and 5 is a supernatant of the recombinant adipose-derived stem cell group.

The cell supernatants were respectively extracted from the group of recombinant adipose-derived stem cells and the blank group, filtered and concentrated through an ultracentrifugation column, by Western blot, the expression of the hFIX protein was detected in the group transfected with viruses carrying the hFIX gene, while no expression of the hFIX protein was detected in the blank group (FIG. 8).

The supernatants of the aforementioned three groups of adipose-derived stem cells were respectively extracted, filtered and concentrated through the ultracentrifugation column, and then the specimen (i.e., the filtered cell supernatant) was sent to Tianjing institute of hematology for detection of hFIX activity (FIX:C). The results showed that, the supernatant of the group transfected with viruses carrying the hFIX gene had a FIX:C of 8.5%, while the other two groups had FIX:C<1%.

When the FIX:C<1%, it could be diagnosed as serious hemophilia, and the cells transfected with the target gene in vitro expressed FIX:C up to 8.5%, which is sufficient to convert the serious hemophilia into mild hemophilia. The amount of hFIX in the cell cultural supernatant was detected with an hFIX ELISA kit, and the results were shown in Table 1.

TABLE 1

| Cell supernatant FIX:Ag (ng/($10^6$ cell · 24 h)) at different times after transfection of ADSCs by ELISA assay | | | |
|---|---|---|---|
| Time | 1 d | 3 d | 9 d |
| FIX:Ag | 21.33 ± 3.93 | 12.63 ± 0.86 | 12.63 ± 2.36 |

It could be seen from Table 1 that, the hFIX protein could be effectively secreted on the 1st day after the ADSCs were transfected with the hFIX gene, and the hFIX protein could be continuously secreted on the 3rd and 9th days after the transfection, but the secretion amount was decreased.

It can be seen from the Embodiments that, an adenovirus carrying an hFIX gene is transfected into an adipose-derived stem cell, and the recombinant adipose-derived stem cell obtained after the transfection can express an hFIX protein.

The foregoing descriptions are only preferred implementation manners of the present invention. It should be noted that for a person of ordinary skill in the art, several improvements and modifications may further be made without departing from the principle of the present invention. These improvements and modifications should also be deemed as falling within the protection scope of the present invention.

What is claimed is:

1. A recombinant method of obtaining a recombinant adipose-derived stem cell, comprising:
    upon reaching 80% confluency of adipose-derived stem cells, mixing the adipose-derived stem cells with an adenovirus carrying an hFIX gene to transfect the adipose-derived stem cells to obtain the recombinant adipose-derived stem cell
    wherein, a titer of the adenovirus carrying the hFIX gene before mixing is $1.26 \times 10^{10}$ pfu/mL, a MOI is 300 after mixing.

2. The recombinant method according to claim 1, wherein when a primary adipose-derived stem cell is passed to the 3rd generation, transfecting the cells of the 3rd generation with an adenovirus carrying the hFIX gene.

3. The recombinant method according to claim 1, wherein the transfection is conducted under 5% $CO_2$.

4. The recombinant method according to claim 1, wherein the adipose-derived stem cell expresses CD29 and CD90, and does not express CD45.

5. The recombinant method according to claim 1, wherein the transfection conditions comprise:
    a transfection temperature in a range of 35-40° C., and the transfection time is 24-72 h.

6. The recombinant method according to claim 5, wherein the transfection is conducted under 5% $CO_2$.

* * * * *